United States Patent
Lin et al.

[11] Patent Number: 5,964,809
[45] Date of Patent: Oct. 12, 1999

[54] POLYETHERETHERKETONE (PEEK) RETAINING RING FOR AN ACETABULAR CUP ASSEMBLY

[75] Inventors: Ruey Y. Lin, New City, N.Y.; Ashok K. Chopra, Morris Plains, N.J.; Allen P. Levine, Brooklyn, N.Y.; Bernard Silverstein, North Bergen, N.J.

[73] Assignee: Howmedica Inc., New York, N.Y.

[21] Appl. No.: 08/907,147

[22] Filed: Aug. 6, 1997

Related U.S. Application Data

[62] Division of application No. 08/600,660, Feb. 13, 1994, Pat. No. 5,782,930.

[51] Int. Cl.⁶ .................................................. A61F 2/34
[52] U.S. Cl. ................................................................ 623/22
[58] Field of Search ................................. 264/257, 165, 264/328.1, 572, DIG. 61, 83; 425/542, 500

[56] References Cited

U.S. PATENT DOCUMENTS

| | | |
|---|---|---|
| 4,676,798 | 6/1987 | Noiles . |
| 5,740,893 | 4/1998 | Yamamoto ................................ 192/45 |

FOREIGN PATENT DOCUMENTS

| | | |
|---|---|---|
| 0 638 299 | 2/1995 | European Pat. Off. . |
| 0 648 478 | 4/1995 | European Pat. Off. . |
| 442044 | 12/1994 | Germany . |
| 295 13 619 | 12/1995 | Germany . |

*Primary Examiner*—David J. Isabella
*Assistant Examiner*—John M. Black
*Attorney, Agent, or Firm*—Joseph J. Kaliko

[57] ABSTRACT

A prosthetic acetabular cup assembly, for receiving a ball attached to a femur, including components interlocked via a locking mechanism that includes a retaining ring fabricated at least in part using a polyaryletherketone material, such as PEEK. The locking mechanism is designed to meet predefined constraints such as assuring that substantially all motion is eliminated between assembled parts, assuring further that push-in/pull-out forces of assembly are within generally accepted industry standards, etc. Further aspect of the invention are directed to (a) the form and composition of the locking mechanism per se, such as locking mechanisms including a retaining ring fabricated at least in part using a polyaryletherketone material, where the shape of the retaining ring and manner in which it cooperates with the other components in the cup assembly results in a locking mechanism that satisfies the aforementioned constraints; (b) processes for fabricating specific types of retaining rings for use in securing the components of an acetabular cup assembly; and (c) to locking rings per se made utilizing polyaryletherketone material and composites including a polyaryletherketone material.

9 Claims, 9 Drawing Sheets

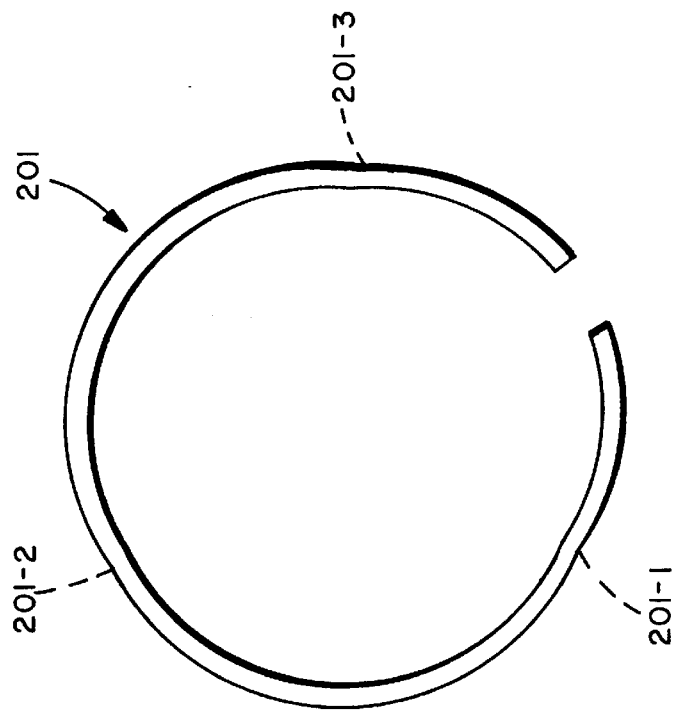
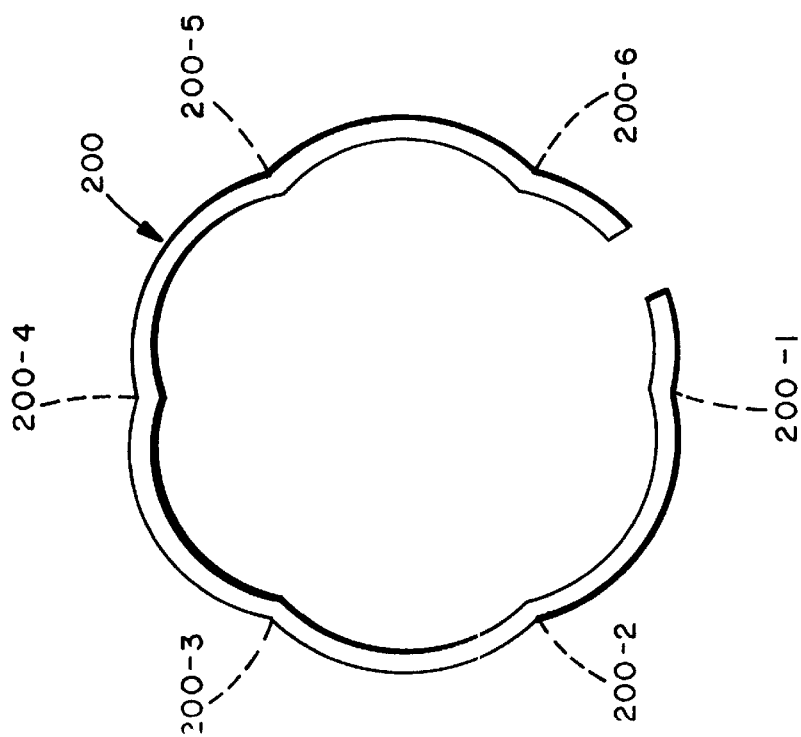
FIG. 2

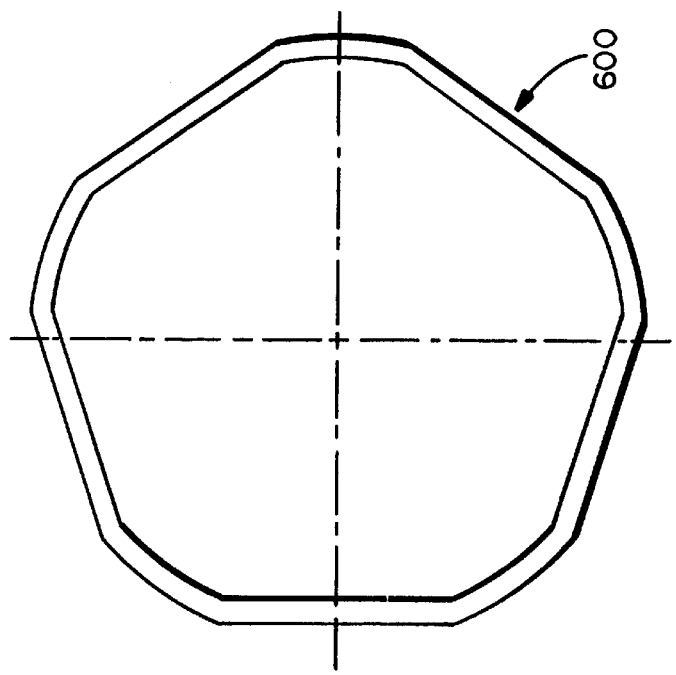
FIG. 6
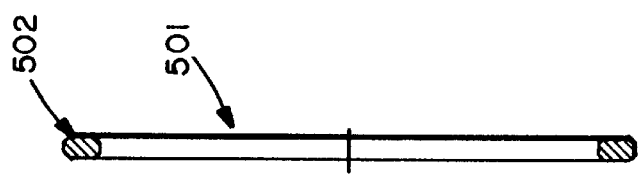
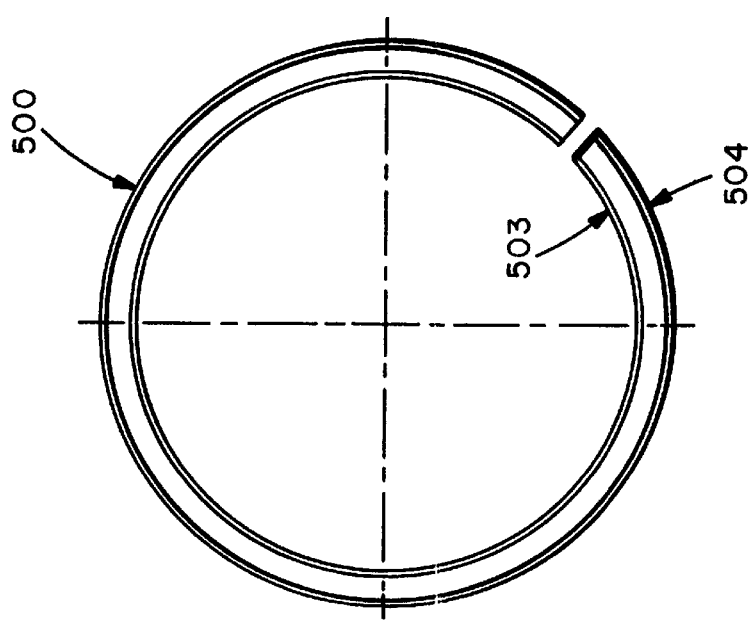
FIG. 5

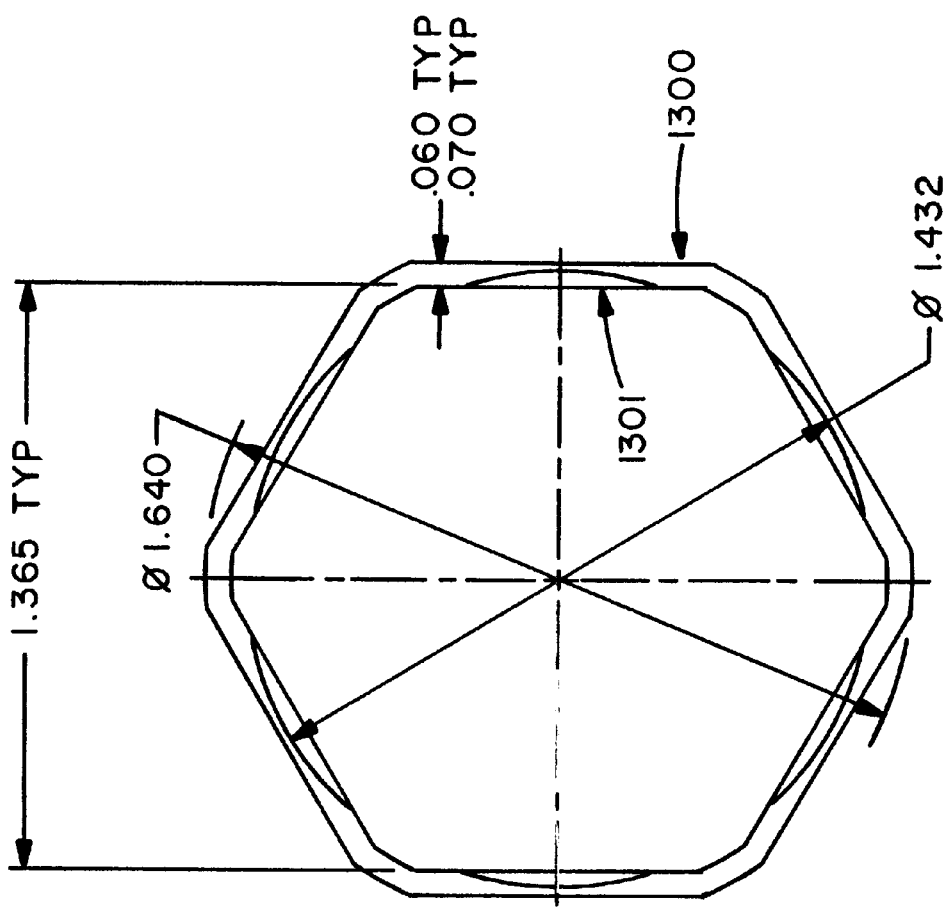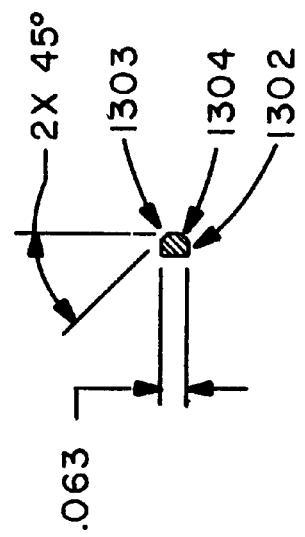
FIG. 13

POLYETHERETHERKETONE (PEEK) RETAINING RING FOR AN ACETABULAR CUP ASSEMBLY

This application is a division of application Ser. No. 08/600,660, filed Feb. 13, 1997, now U.S. Pat. No. 5,782,930.

BACKGROUND OF THE INVENTION

1. Field of the Invention

The invention relates generally to hip prosthesis assemblies for replacing a natural hip socket; the form and composition of locking mechanisms used in such assemblies to secure the attachment of assembly components; and to processes for fabricating specific types of locking mechanisms including retaining rings per se, contemplated by the invention.

More particularly, a first aspect of the present invention relates to a prosthetic acetabular cup assembly for receiving a ball attached to a femur. The components of the assembly (an insert bearing component and an outer shell component, both to be described in greater detail hereinafter) are, according to a preferred embodiment of the invention, interlocked via a locking mechanism that includes a retaining ring fabricated at least in part using polyaryletherketone material, such as PEEK.

The locking mechanism used in such assemblies may take any one of a number of shapes that are useful for securing assembly components. Constraints influencing locking mechanism design include insuring that substantially all motion is eliminated between assembled parts, insuring further that push-in/pull-out forces of assembly are within generally accepted industry standards, etc.

A further aspect of the invention is directed to the form and composition of the locking mechanism per se. More particularly, various specific locking mechanisms fabricated using polyaryletherketone materials have been identified which have been found to have advantageous shapes for meeting the aforementioned constraints For example, according to one embodiment of the invention the locking mechanism includes a hex-shaped retaining ring having an inside radial chamfer, where the retaining ring is a composite fabricated at least in part using PEEK combined with a reinforcing material, e.g., carbon fibers with the reinforcing material being added to the PEEK matrix in order to reinforce the composite ring (e.g., to strengthen and add rigidity to the ring).

Still further aspects of the invention are, as indicated hereinabove, directed to processes for fabricating specific types of retaining rings for use in securing the components of an acetabular cup assembly; and to locking rings per se made utilizing polyaryletherketone material.

2. Description of the Related Art

It is known to provide an acetabular cup assembly, including a metal shell component for attachment to an acetabulum, to replace the natural socket; and to provide a polymer bearing component which is inserted into the shell to provide a hemispherical bearing surface for receiving a femur ball prosthesis element. Often, the polymer bearing component (also referred to herein as an "insert" component) is nonsymmetrical and includes a built up lip around a portion of the hemispherical bearing surface to help prevent dislocation of an installed femur ball from the hemispherical bearing surface.

During installation of the acetabular cup assembly, the shell component is first secured to the acetabulum. When a surgeon installs the bearing component, the surgeon selects an orientation of the bearing with respect to the shell component to align the lip of the nonsymmetrical bearing component in the most advantageous position to reduce the likelihood of dislocation of the femur ball.

Therefore, it is desirable to produce an acetabular cup assembly in which (a) the bearing component can be easily attached to the shell component in a large number of selected orientations to provide the maximum degree of flexibility for the surgeon using only a push-in force within some predefined range; and (b) the retention mechanism (for interlocking the shell and insert, also referred to herein as the "locking mechanism") allows the bearing component to be easily oriented and easily installed (as indicated hereinbefore); and easily removed by the surgeon, if necessary, using only a pull-out force within some predefined range.

The installed bearing component must also be secured to the shell component by a retention force (and associated means for inducing such force) that is strong enough to prevent rotation or dislocation of the bearing component from the shell component when the cup assembly is completed and being used as intended as a hip prosthesis device, i.e., after having been installed by the surgeon within the shell at the desired orientation.

An example of prior art addressing some of the aforementioned desirable aspects of an acetabular cup assembly and locking mechanism therefore, is U.S. Pat. No. 5,049,158, issued on Sep. 17, 1991, to Engelhardt et al. U.S. Pat. No. 5,049,158 is hereby incorporated by reference.

The objectives of the incorporated reference (many of which are shared by the present invention) included (a) providing a retention mechanism for retaining a bearing component situated at any selected orientation inside a shell component which does not rely on the physical properties of the bearing component; (b) reducing the loading of forces on an outer lip or flange of the bearing component after the hip prosthesis is installed in a patient; (c) preventing rotation of the bearing component relative to the shell component after insertion of the bearing component into the shell component in a desired orientation; and (d) providing a self adjusting locking mechanism which retains the bearing component inside the shell component despite possible shrinkage of the bearing component after installation.

The incorporated reference met these objectives via its teaching of a prosthetic acetabular cup assembly that includes a single piece bearing component having an inner bearing surface for receiving a ball attached to a femoral prosthesis and an outer surface. The assembly includes a shell component for attachment to an acetabulum to replace a natural hip socket and has an inner surface defining a cavity for receiving the bearing component therein.

According to the incorporated reference, a formed wire is situated in an arcuate groove that is part of the shell component. The formed wire is configured so that a portion of the wire extends radially inwardly from the arcuate groove of the shell component to engage a corresponding, axially aligned, arcuate groove formed in the bearing component to retain the bearing component inside the shell component without the use of attachment screws or the like.

Furthermore, according to the incorporated reference, anti-rotation lugs are formed on the inner surface of the shell component to cut into the outer surface of the bearing component as the bearing component is inserted into the shell component to prevent rotation of the bearing component relative to the shell component.

The incorporated reference goes on to teach the use, according to a preferred embodiment of the invention taught, of a serpentine shaped lock wire to interconnect and lock together the aforementioned bearing and shell components; with the lock wire preferably being made of cobalt chrome material that is shaped by conventional wire forming techniques. The resulting metal wire is, according to the reference, optionally heat treated to increase its strength. Titanium is also suggested by Engelhardt et al. as an alternate metal for fabricating the lock wire.

U.S. Pat. No. 4,380,090, issued Apr. 29, 1983, to Ramos, is another example of prior art which teaches the use of locking rings for an acetabular cup assembly. In particular, Ramos teaches that the lock ring for an acetabular cup assembly is "preferably made of a resistant metal such as Vitallium or stainless steel".

Using metal wire rings as part of a locking mechanism for interlocking components of an acetabular cup assembly, as taught in the prior art exemplified by the patents referred to hereinabove, is inherently problematic. For example, as those skilled in the art will readily appreciate, if the rings are made too thick they are stiff and not easy to work with; if the rings are made to thin they are "sloppy", that is they do not always retain their intended shape, spring capacity, etc.

Further problems with locking mechanisms for acetabular cup assemblies that employ metallic retaining rings include the prospect of unacceptably high push-in and/or pull-out forces being required when respectively assembling or trying to purposely disengage assembly components. For example, in the experiments to be described hereinafter it was found that a pull out force in excess of 1,500 pounds was required for Vitallium (™) rings of approx. 0.050" in diameter.

Further yet, use of metallic wire lock rings, such as the Vitallium rings preferred by the aforementioned Ramos reference, etch, are known to be problematic because of certain inherently difficult and/or expensive process steps required when working with such material. Examples of such process steps include those steps needed to perform the inherently difficult task of converting straight wire into a desired wavy structure; steps needed to heat treat metallic wire retaining rings to increase their strength, etc.

Alternative materials for making lock rings, such as silicone and Ultra-High Molecular Weight Polyethylene (UHMWPE), are also known in the art. However, many of these materials suffer from problems of their own. For example, both silicone and UHMWPE have inconsistent problems with a wide spread of push-in and push-out strengths, problems related to the shell/insert interface being too loose when these materials are used to fabricate the retaining ring, etc. Several of these problems were demonstrated in experiments referred to hereinafter, in the Detailed Description of the invention, where polyethylene was used to fabricate experimental retaining rings.

For all of the reasons set forth hereinabove, it would be desirable to provide an acetabular cup assembly design which is easy to use by the surgeon; is simple to put together and take apart as needed; and is made up of components that are easy to fabricate and replicate in mass at low cost.

As indicated hereinbefore, this desire includes being able to provide: (a) an acetabular cup assembly in which the bearing component can be easily attached to the shell component in a large number of selected orientations to provide the maximum degree of flexibility for the surgeon using only a push-in force within some predefined range; (b) a locking mechanism for use in such assemblies (for interlocking the shell and insert), which allows the bearing component to be easily oriented, easily installed and be easily removed by the surgeon, if necessary, using only a pull-out force within some predefined range; and (c) an acetabular cup assembly in which the bearing component can be secured to the shell component by a retention force (and associated means for inducing such force) that is strong enough to prevent rotation or dislocation of the bearing component from the shell component when the cup assembly is completed (after insertion of the bearing component into the shell component in a desired orientation) and being used as intended as a hip prosthesis device.

Furthermore, in view of the prior art discussed hereinabove, it would be particularly desirable to provide a locking mechanism for an acetabular cup assembly which includes a retaining ring that is made from a material that is strong, easy to machine and does not require the performance of the aforementioned wire shaping and/or heat treatment ring fabrication process steps.

Further yet, it is desirable to provide a locking mechanism for an acetabular cup assembly, that includes a retaining ring that is made from a material that allows the rings to be mass produced by, for examples an injection molding process to realize objectives of being able to minimize locking mechanism fabrication costs, assure consistency in the locking mechanism fabrication process and assure the quality of the components produced by such processes, etc.

Further still, it would be desirable to provide an acetabular cup assembly and a locking mechanism therefore, for use in such assembly to retain the bearing component inside the shell component after installation, which includes a retaining ring that is formed using materials that exhibit consistent push-in and pull-out forces; and result in assemblies that do not experience shell/insert toggle.

In view of the teachings of the incorporated Engelhardt et al. patent, which illustrates the present state of the art, it would be desirable to provide a locking mechanism that prevents rotation of assembly components and substantially eliminates motion between assembly components without having to machine or otherwise form separate means (like Engelhardt's lugs) to prevent such rotation and/or other motion.

Finally, it would be desirable to provide processes per se for fabricating the aforementioned desirable locking mechanisms and retaining rings, particularly those locking mechanisms and retaining rings that are suitable for incorporation into acetabular cup assemblies.

SUMMARY OF THE INVENTION

In view of the foregoing, it is a general object of the invention to provide an acetabular cup assembly in which the bearing component can be easily attached to the shell component in a large number of selected orientations to provide the maximum degree of flexibility for the surgeon using only a push-in force within some predefined range.

It is a further object of the invention to provide a locking mechanism for use in such assemblies (for interlocking the shell and insert), which allows the bearing component to be easily oriented, easily installed and be easily removed by the surgeon, if necessary, using only a pull-out force within some predefined range.

Still further, it is an object of the invention to provide an acetabular cup assembly in which the bearing component can be secured to the shell component by a retention force (and associated means for inducing such force) that is strong enough to prevent rotation or dislocation of the bearing component from the shell component when the cup assembly is completed (after insertion of the bearing component into the shell component in a desired orientation) and being used as intended as a hip prosthesis device.

Yet another object of the invention is to provide means for retaining a polymeric (or composite) bearing component (the insert) inside an acetabular metal shell without the use of attachment screws or metallic lock rings.

Furthermore, it is an object of the invention to provide a locking mechanism for an acetabular cup assembly, including a retaining ring therefore, that can be fabricated using a material that is strong, easy to machine and does not require the performance of the aforementioned wire shaping and/or heat treatment ring fabrication process steps.

Further still, it is an object of the invention to provide a locking mechanism for an acetabular cup assembly, including a retaining ring therefore, that can be fabricated using an injection molding process on production quantities to reduce the cost, assuring the consistency and quality of the components produced, etc.

Still another object of the invention is to provide an acetabular cup assembly and a locking mechanism therefore, for use in such assembly to retain the bearing component inside the shell component after installation, which includes a retaining ring that is formed using materials that exhibit consistent push-in and pull-out forces; and result in assemblies that do not experience shell/insert toggle.

It is also an object of the invention to provide a locking mechanism that prevents rotation of assembly components and substantially eliminates motion between assembly components without having to machine or otherwise form separate means intended to prevent such rotation and/or other motion.

Finally, it is an object of the invention to provide processes for fabricating the aforementioned desirable locking mechanisms and retaining rings.

According to one aspect of the invention, alternative materials have been identified for use in fabricating retaining rings, particularly retaining rings used as part of locking mechanisms that secure the components of an acetabular cup assembly.

One such material is PEEK, which is a member of the polyaryletherketone polymer family. The polymer PEEK has excellent mechanical properties and machinability Evaluations of this material, discussed in more detail hereinafter in the Detailed Description of the invention, have shown that PEEK retaining rings with tight tolerance can be easily machined to fit into the groove in the insert and the metal shell backing; and that no rocking motion was noticed in the assembly (presumably due to the better dimension fit between the ring, insert and shell).

Composite materials, such as PEEK reinforced with carbon fibers have also been identified as being suitable for meeting the aforestated objectives.

The invention may best be appreciated by those skilled in the art by considering various aspects thereof to be set forth immediately hereinafter. In particulars one aspect of the invention is directed to an acetabular cup assembly for a femur ball, comprising: (a) an insert bearing component for receiving the femur ball; (b) an outer shell component, for attachment to an acetabulum to replace a natural hip socket, including a cavity for receiving the insert bearing component therein; and (c) a locking mechanism for interlocking the insert into the outer shell, the locking mechanism comprising a retaining ring that is fabricated at least in part using polyaryletherketone material.

According to a preferred embodiment of this first aspect of the invention, the polyaryletherketone material is PEEK and the ring is made entirely of PEEK (i.e., is a 100% PEEK ring). Furthermore, in accordance with alternate embodiments of the invention, the PEEK may be reinforced using a material like carbon fiber.

According to another aspect of the invention, a prosthetic acetabular cup assembly for receiving a ball attached to a femur, comprises: (a) an insert bearing component, including an inner bearing surface for receiving the ball and an outer surface formed to include an arcuate groove therein; (b) an outer shell component for attachment to an acetabulum to replace a natural hip socket, the outer shell component including an inner surface defining a cavity for receiving the insert bearing component therein, the inner surface of the outer shell component being formed to include an arcuate groove therein at a location that is axially aligned with the arcuate groove formed in the insert bearing component; and (c) a locking mechanism that when located in the arcuate groove of the outer shell component will engage the insert bearing component, upon insertion of the insert bearing component into the outer shell component, by extending into the arcuate groove located on the outer surface of the insert bearing component to thereby retain the insert bearing component inside the outer shell component, the locking mechanism comprising a retaining ring that is fabricated at least in part using polyaryletherketone material (e.g., PEEK).

A further aspect of the invention is directed to a locking mechanism per se for interlocking components of an acetabular cup assembly, the locking mechanism comprising a retaining ring that is fabricated at least in part using polyaryletherketone material (like PEEK); together with a reinforcing material (like carbon fiber). The locking mechanism is further defined, according to this aspect of the invention, to include a retaining ring formed (using the materials described hereinabove) to simultaneously fit into grooves located in the components being interlocked.

Further variants on (alternate embodiments of) this aspect of the invention (directed to the locking mechanism per se) encompass, by way of example and without limitation except as specifically recited in the claims, the use of (as part of such mechanism) a closed retaining ring; a "split" (open) retaining ring; retaining rings that are circular in shape; retaining rings that have a polygon shape (such as penta shaped and hex shaped rings); retaining rings that are chamfered in any one of a variety of ways; retaining rings formed to included any number of lobes; and/or rings combining any number of the above features with the object of achieving push-in and pull-out forces within a predefined range, substantially eliminating cup assembly component motions etc., as discussed hereinbefore.

Furthermore, according to this aspect of the invention (directed to the locking mechanism apparatus per se) the retaining rings used may be fabricated via a machining process using extruded polyaryletherketone stock; and as a preferred alternative, the rings are contemplated as being a product of an injection molding process.

Another aspect of the invention is directed to a process per se for fabricating a locking mechanism to secure components of an acetabular cup assembly, the assembly including an insert bearing component for receiving a femur ball and an outer shell component, for attachment to an acetabulum to replace a natural hip socket, including a cavity for receiving the insert bearing component therein, comprising the steps of: (a) forming a first arcuate groove on the outer surface of the insert bearing component; (b) forming a second arcuate groove on the inner surface of the outer shell component at a location that is axially aligned with the arcuate groove formed in the insert bearing component; and (c) fabricating a retaining ring for interlocking the insert into the outer shell, the retaining ring being formed at least in part using polyaryletherketone. Alternative embodiments of this process contemplate utilizing a machining process to form the ring; and utilizing an injection molding process to form the ring.

The locking mechanism fabrication process contemplated by this aspect of the invention further comprehends (again, by way of example without limitation except as expressly recited in the claims) using PEEK to form the retaining ring; forming the ring (according to one embodiment of the invention) such that the finished ring, when located simultaneously in the first arcuate groove and the second arcuate groove to thereby interlock the insert and outer shell, has a finite number of contact points on both the insert and on the outer shell; forming the ring (in an alternate embodiment of the invention) such that the finished ring is circular in shape; forming the retaining ring as a split ring; forming the retaining ring as a closed ring; combining the polyaryletherketone with a reinforcing material (such as carbon fiber) etc.

Yet another aspect of the invention is directed to a process for fabricating a retaining ring for an acetabular cup assembly that includes (a) an insert bearing component having an inner bearing surface for receiving the ball and an outer surface formed to include an arcuate groove therein and (b) an outer shell component for attachment to an acetabulum to replace a natural hip socket, the outer shell component including an inner surface defining a cavity for receiving the insert bearing component therein, the inner surface of the outer shell component being formed to include an arcuate groove therein at a location that is axially aligned with the arcuate groove formed in the insert bearing component, comprising the steps of: (a) creating a mold for the retaining ring having a predefined shaped which allows the ring, when formed, to be inserted into the arcuate groove of the outer shell component and simultaneously engage the insert bearing component, upon insertion of the insert bearing component into the outer shell component, by extending into the arcuate groove located on the outer surface of the insert bearing component; and (b) injecting a polyaryletherketone material into the mold.

Alternate embodiments of this aspect of the invention include processes where the polyaryletherketone is PEEK; forming the ring such that the finished ring is circular in shape; forming the retaining ring as a split ring; forming the retaining ring as a closed ring; combining the polyaryletherketone with a reinforcing material (such as carbon fiber), etc.

Still another aspect of the invention is directed to a process for fabricating retaining rings used in acetabular cup assemblies for interlocking the components thereof, comprising the steps of: (a) forming a mold to create retaining rings having a predetermined shape enabling each such ring to extend simultaneously into a pair of grooves, each located in one of a pair of components being interlocked, using only a push-in force within a predefined range of push-in forces to combine the components and the ring; and (b) injecting polyaryletherketone material into the mold as part of an injection molding process to create the retaining rings having the predetermined shape.

Furthermore, according to this aspect of the invention, the predetermined shape is such that only a predetermined amount of pull-out force within a predefined range of pull-out forces is required to separate the combination of said pair of components and ring once joined.

Finally, certain other specific aspects of the invention are directed to a retaining ring per se, fabricated at least in part using polyaryletherketone material (preferably reinforced PEEK) where one application of the ring is for use in an acetabular cup assembly; a PEEK retaining ring per se, used as part of a locking mechanism for interlocking components of an acetabular cup assembly; and a composite PEEK/carbon fiber retaining ring per se, used as part of a locking mechanism for interlocking components of an acetabular cup assembly.

The invention features locking mechanisms including retaining rings and retaining rings per se, made from materials that can be easily machined; and are suitable for use in injection molding processes to lower ring production costs, etc. These locking mechanisms and retaining rings are particularly useful in acetabular cup assemblies.

Furthermore, the invention features acetabular cup assemblies incorporating the aforementioned component locking mechanisms and/or retaining rings; and process for fabricating locking mechanisms and retaining rings meeting the aforestated objectives.

Further still, the invention features acetabular cup assemblies in which the bearing component can be easily attached to the shell component in a large number of selected orientations to provide the maximum degree of flexibility for the surgeon; locking mechanisms (including retaining rings) for use in such assemblies for interlocking the shell and insert, which allow the bearing component to be easily oriented, easily installed and be easily removed by the surgeon; acetabular cup assemblies in which the bearing component can be secured to the shell component by a retention force (and associated means for inducing such force) that is strong enough to prevent rotation or dislocation of the bearing component from the shell component when the cup assembly is completed, without the use of attachment screws or metallic lock rings; and acetabular cup assemblies that include locking mechanisms (which further include retaining rings) formed using materials that exhibit consistent push-in and pull-out forces, prevent rotation of assembly components and substantially eliminate motion between assembly components without having to machine or otherwise form separate means intended to prevent such rotation and/or other motion.

These and other objects, embodiments and features of the present invention and the manner of obtaining them will become apparent to those skilled in the art, and the invention itself will be best understood by reference to the following Detailed Description read in conjunction with the accompanying Drawing.

BRIEF DESCRIPTION OF THE DRAWING

FIG. 2 depicts a top view of a two versions of a circular Vitallium wire retaining ring; one version having six lobes as shown on the left hand side of FIG. 2 and the other version having three lobes as shown on the right hand side of FIG. 2. Both rings are "closed" (i.e., form a continuous loop).

FIG. 5 depicts a top view of an open ("split") circular retaining ring, fabricated at least in part using a polyaryletherketone material (shown on the left hand side of FIG. 5); and an exemplary cross sectional view of the aforementioned ring indicating the ring is chamfered.

FIG. 6 depicts a top view of a closed penta shaped retaining ring fabricated at least in part using a polyaryletherketone material.

FIG. 9 also depicts an exemplary cross sectional view of the aforementioned ring depicting the chamfer.

FIG. 13 depicts a top view of a closed hex shaped retaining ring with an inside radial chamfer, where the ring is fabricated at least in part using a polyaryletherketone material (shown on the right hand side of FIG. 13); and an exemplary cross sectional view of the aforementioned ring depicting the chamfer (shown on the left hand side of FIG. 13).

DETAILED DESCRIPTION

The invention will now be described with reference to a set of experiments conducted on various acetabular cup component locking mechanisms, including retaining rings fabricated using Vitallium wire, Ultra-High Molecular weight Polyethylene (UHMWPE) and polyaryletherketone material, to demonstrate by way of example quantifiable advantages of using a polyaryletherketone, such as PEEK, in realizing the aforestated objects of the invention. The experiments conducted and results observed are in no way intended to limit the scope or spirit of the invention which is intended to be limited only by the claims appended hereto.

The object of the experiments conducted was to develop a suitable retaining ring for locking a composite acetabular cup (the aforementioned "insert" component) into an outer shell. The experiments were conducted using Vitalock (™) shells, commercially available from the assignee of the present invention. A 50 mm/28 mm P3 shell was used for this design. The insert used in combination with the shell had an o-ring type groove incorporated therein for locking the insert into the shell. The use of such a groove as part of a locking mechanism in an acetabular cup assembly is known in the prior art, as exemplified by the teachings of the incorporated reference where the bearing component is shown to include such groove (also referred to in the incorporated reference and elsewhere herein as an "arcuate groove" which is preferably axially aligned with a corresponding groove inside the shell component into which the bearing component is inserted).

Furthermore, for the experiments conducted it was assumed that the insert had to be face loaded on its flange area; substantially all motion between assembled parts had to be eliminated; and it was an object of the experiments to find a locking mechanism and retaining ring for which the push-in/pull-out forces of the cup assembly were within industry standards understood by those skilled in the art.

Figure 1:
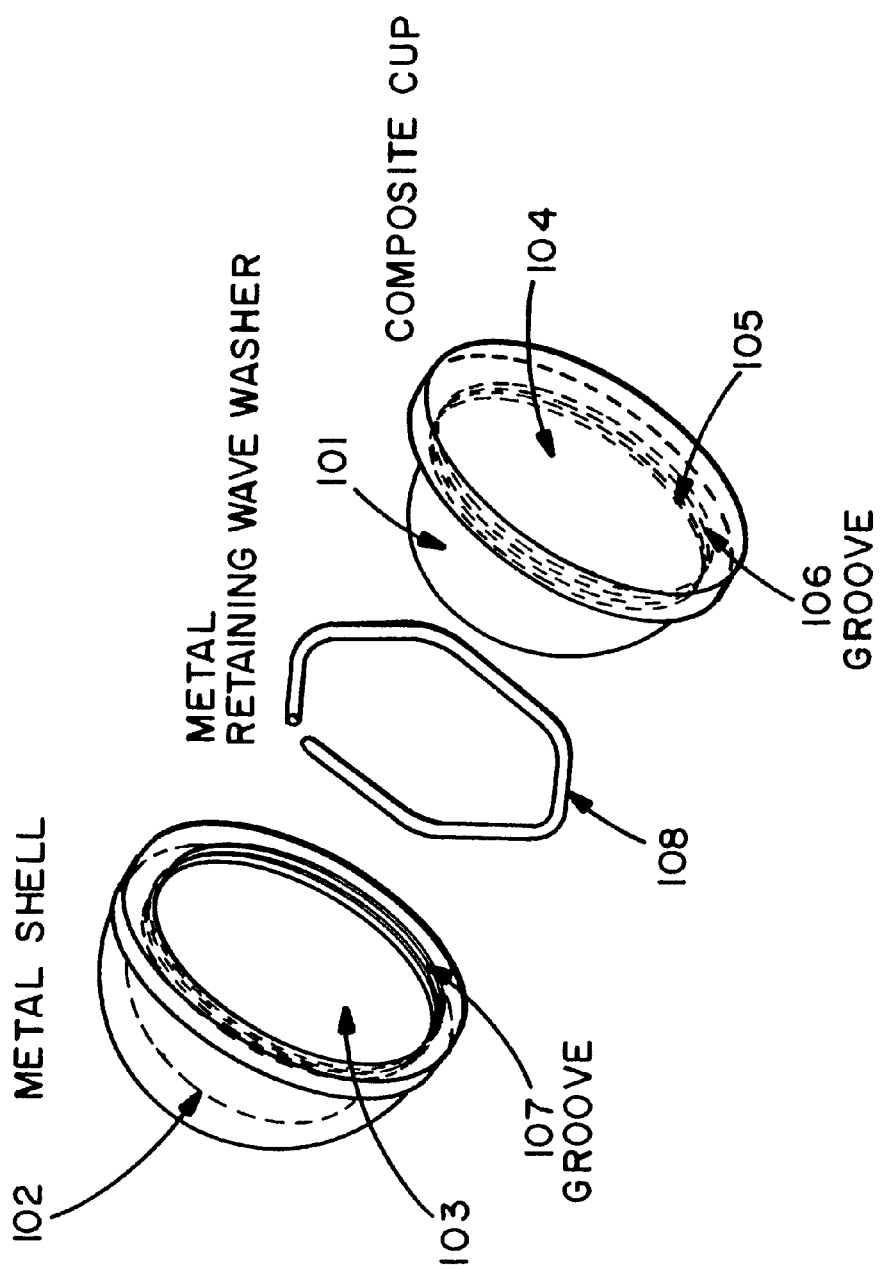
FIG. 1 depicts an exploded view of a prosthetic acetabular cup assembly in which the instant invention may be advantageously used.

Reference should now be made to FIG. 1 which depicts a prosthetic acetabular cup assembly 100 for a femur ball that includes insert bearing component 101 for receiving the femur ball; and outer shell component 102 which may be attached to an acetabulum to replace a natural hip socket, with the depicted outer shell component 102 including cavity 103 for receiving insert bearing component 101.

Insert bearing component 101 is further shown in FIG. 1 to include an inner bearing surface 104 for receiving the ball and an outer surface 105 formed to include arcuate groove 106 therein. Inner surface 103 of outer shell component 102 is also shown to include an arcuate groove (107) formed therein at a location that is axially aligned with arcuate groove 106 formed in insert bearing 101.

The instant invention focuses on the form and composition of locking mechanisms that may be used to interlock acetabular cup assembly components, such as insert bearing component 101 and outer shell component 102 depicted in FIG. 1. An exemplary prior art mechanism used for this purpose (which sits, after assembly, simultaneously in arcuate grooves 106 and 107) is shown at 108 in FIG. 1, in the form of a metallic retaining ring wave washer.

A chronological development sequence ensued in which three different ring materials were researched and tested, Vitallium (™), Ultra-High Molecular Weight Polyethylene (UHMWPE), and a polyaryletherketone material, specifically, PEEK.

Reference should now be made to FIG. 2 which, as indicated hereinbefore, depicts a top view of a two versions of a circular Vitallium wire retaining ring; one version having six lobes (designated as the lobes between ring segments 200-1 to 200-2; 200-2 to 200-3; 200-3 to 200-4; 200-4 to 200-5; 200-5 to 200-6; and 200-6 to 200-1), as shown on the left hand side of FIG. 2 at 200; and the other version having three lobes (designated as the lobes between ring segments 201-1 to 201-2; 201-2 to 201-3; and 201-3 to 201-1), as shown on the right hand side of FIG. 2 at 201. Both rings are "closed" (i.e., form a continuous loop).

Vitallium rings, such as those depicted in FIG. 2 at 200 and 201, were designed and experiments conducted which verified Vitallium can be used as a spring lock mechanism. However, the ability for Vitallium rings to retain their springing capability on a long term basis remains unknown and is a concern for a lock mechanism being employed in the human body as part of an acetabular cup assembly.

It was determined via the experiments conducted that Vitallium can be formed or cast for production quantities. Exemplary wire diameters used in the experiments were 0.062" and 0.045". Fixtures were developed to form the parts; and samples were made for each lobe design shown in FIG. 2 (i.e., for a rings shaped as shown in FIG. 2 at 200 and 201, respectively), for each of the aforementioned wire diameters.

Testing results for both the three and six lobe variations were similar. The 0.062" wire was to stiff (the wire was too thick); and the 0.045" wire was to sloppy (the wire was too thin).

Samples of 0.055" and 0.050" diameter wire were obtained and rings were tested The further test results showed that although the wire diameters fit nicely into the grooves on the shell and insert; the shell/insert interface was still too loose. A rocking motion was observed in the assembly due to the locking mechanism not functioning properly Of further significance was the fact that push-out strength was very high; in excess of 1,500 pounds, as indicated hereinbefore.

Figure 3:
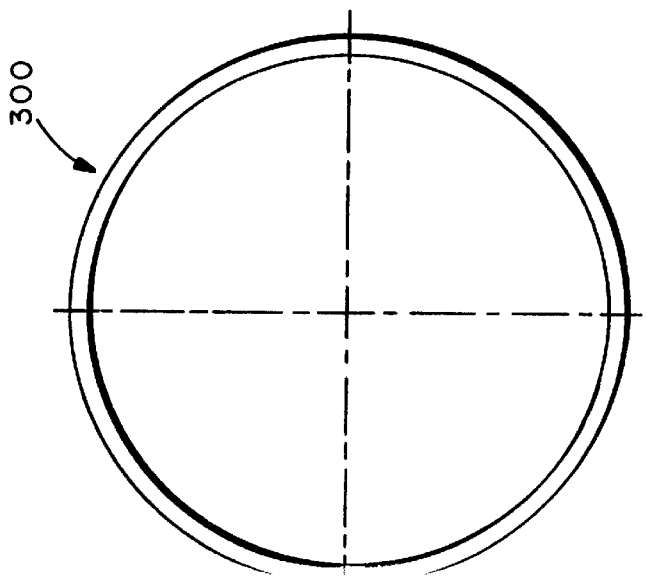
FIG. 3 depicts a top view of a closed circular polyethylene retaining ring (shown on the left hand side of FIG. 3); and an exemplary cross sectional view of the aforementioned ring showing an outside chamfer.

Reference should now be made to FIG. 3 which, as indicated hereinbefore, depicts a top view of a closed circular polyethylene retaining ring (shown on the left hand side of FIG. 3 at 300); and an exemplary cross sectional view of the aforementioned ring (depicted in FIG. 3 at 301) showing an outside chamfer, 302.

Rings made of polyethylene (like the exemplary retaining ring 300 shown in FIG. 3 which was fabricated using UHMWPE), were tested and were found to be thin, dimensionally inconsistent and were not readily amenable for machining (i.e., machinablity was poor). Insertion force requirements were low and a significant amount of shell/insert rocking was noted. As a result of these experiments work on additional polyethylene rings was stopped and a search for an alternate polymeric material lead to the consideration of a polyaryletherketone material, in particular PEEK, as a material from which to fabricate a retaining ring.

It was determined in further experiments that polyaryletherketone material, in particular PEEK, can be easily machined. The further experiments resulted in the rings depicted in FIGS. 4–13 being fabricated and tested with good results being achieved for meeting the aforestated objectives of the invention. These ring designs and experimental results will be set forth hereinafter to demonstrate that locking mechanisms and retaining rings for acetabular cup assemblies, fabricated in part using polyaryletherketone material, meet the aforementioned objectives.

Figure 4:
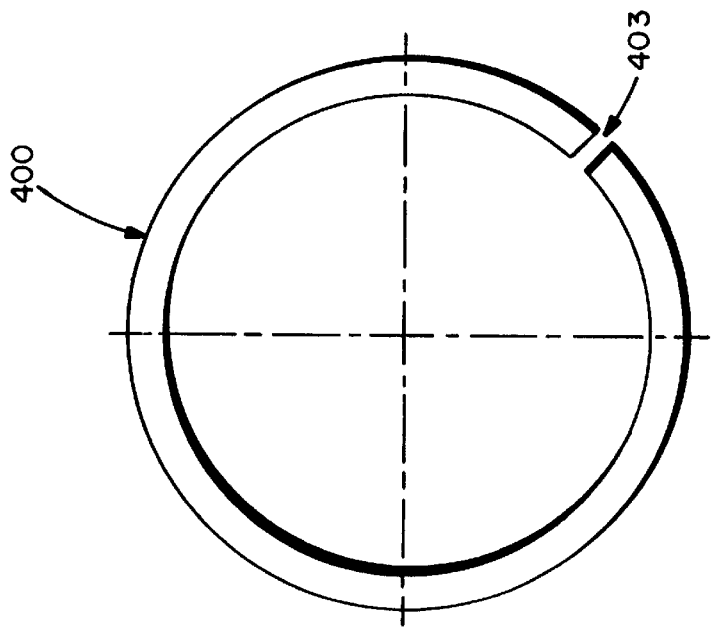
FIG. 4 depicts a top view of an open ("split") circular retaining ring fabricated at least in part using a polyaryletherketone material (e.g., PEEK), shown on the left hand side of FIG. 4; and an exemplary cross sectional view of the aforementioned ring indicating no chamfer.

Reference should now be made to FIG. 4 which, as indicated hereinbefore, depicts a top view of an open ("split") circular retaining ring 400, fabricated at least in part using a polyaryletherketone material (e.g., PEEK), shown on the left hand side of FIG. 4; and an exemplary cross sectional view 401 of the aforementioned ring indicating no chamfer (indicated via reference numeral 402).

Experimental rings of the type depicted in FIG. 4 were fabricated and tested in a first experiment with variety of thicknesses ranging from 0.054" to 0.058". All the rings were split with a small section removed, as shown at 403 in FIG. 4. Push-in forces experienced during this first experiment ranged from 30 kg to greater than 500 kg. Push-out forces required exceeded 500 kg.

A second test performed on the type of ring depicted in FIG. 4, on three additional circular rings, varied from hand assembled to a push-in force requirement of 715 kg; push out force requirements varied from a reading to low to determine to 658 kg. These values were considered to be too high and further experimentation with PEEK retaining ring design continued with the type of ring depicted in FIG. 5.

As indicated hereinbefore, FIG. 5 depicts a top view of an open ("split") circular retaining ring fabricated at least in part using a polyaryletherketone material (an example of such ring is shown at 500 on the left hand side of FIG. 5); and an exemplary cross sectional view of ring 500, shown at 501 in FIG. 5, indicates ring 500 is chamfered. This chamfer feature is depicted in cross sectional view 501 at 502; and is further depicted with reference to ring 500 at 503 (depicting an inside chamfer) and 504 (depicting an outside chamfer).

The performance of PEEK rings like ring 500 (with chamfers like chamfer 503 and chamfer 504 added respectfully to the inside and outside diameters of such circular rings), was compared with similar non-chamfer PEEK rings with various band widths and thickness ranging from 0.060" to 0.066".

Test results indicted circular PEEK retaining rings, with and without chamfers, had inconsistent push-in/push-out results and most of the tested assemblies had shell/insert toggle. It was apparent from this experiment that the chamfering alone was not enough to achieve the desired performance requirements for retaining rings used in acetabular cup assemblies and that further modification would be needed.

A larger sample of twenty four circular PEEK rings were tested, both chamfered and non-chamfered rings. All were hand assembled and very loose with very high push out forces required.

A different concept for the PEEK rings was then tested. The design of the new ring, a top view of which is shown in FIG. 6 as exemplary ring 600, was a closed penta shaped retaining ring fabricated at least in part using a polyaryletherketone material. The penta shaped design which gives five points of contact on the insert and five on the shell. Two such rings were fabricated and tested with the test results showing push-in forces of 5 kg and 5.6 kg for the two tests respectively. Furthermore, the fit of the ring was good and a push-out force of 297 kg. was measured.

Figure 7:
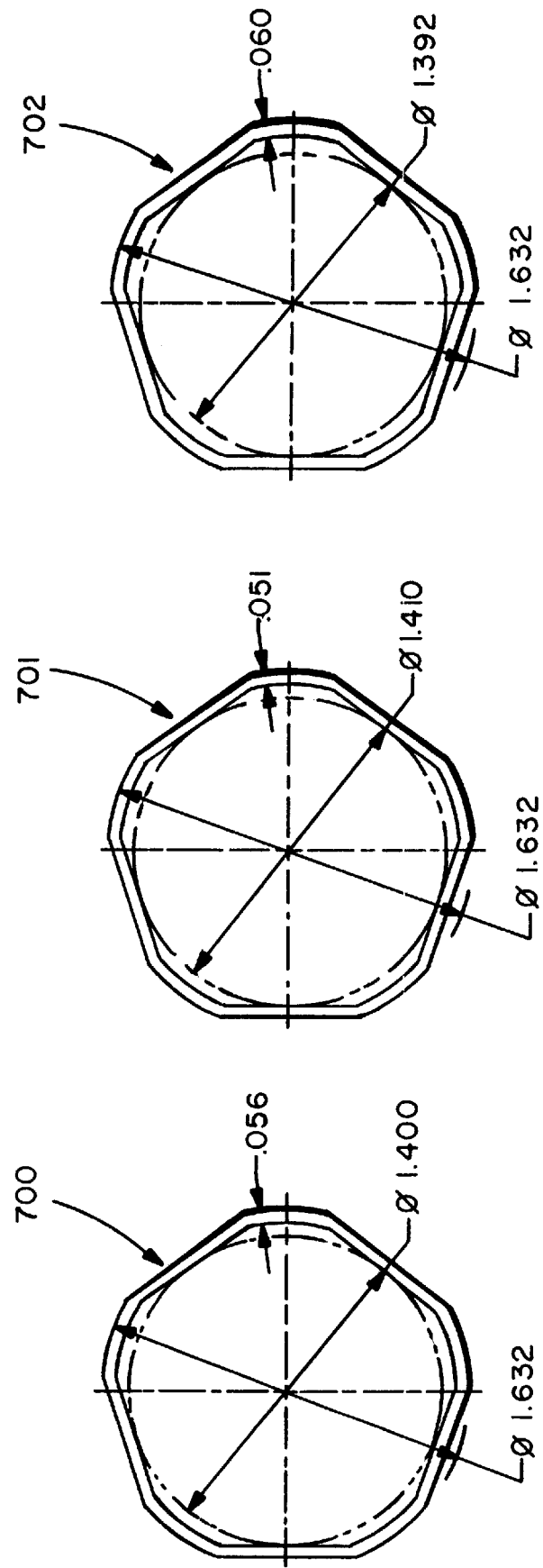
FIG. 7 depicts a top view of three closed penta shaped retaining rings having varying inner diameters and "band widths" (defined as the difference between the outer diameter and the inner diameter of the ring) where each ring is again fabricated at least in part using a polyaryletherketone material.

Six additional penta rings were made with varying band widths. Three of these rings, 700, 701 and 702, are depicted in FIG. 7 which depicts a top view of the three rings. Each of the rings depicted in FIG. 7 is a closed penta shaped retaining ring. Rings 700–702 having varying inner diameters and band widths (examples of which are illustrated in FIG. 7). All of the depicted rings were hand assembled and fabricated at least in part using a polyaryletherketone material for the experiments to be conducted; two of the rings were fabricated with inside chamfers.

Two push-in tests conducted on non-chamfered rings of the type depicted in FIG. 7, recorded required push-in forces of 7.7 kg and 11 kg. All assembled parts had various degrees of toggling. The range of push-out for non-chamfered rings was 240 lbs through 468 lbs. The push-out forces for the two inside chamfered rings were lower as expected, with one test yielding a required push-out force of 29 lbs.

Figure 8:
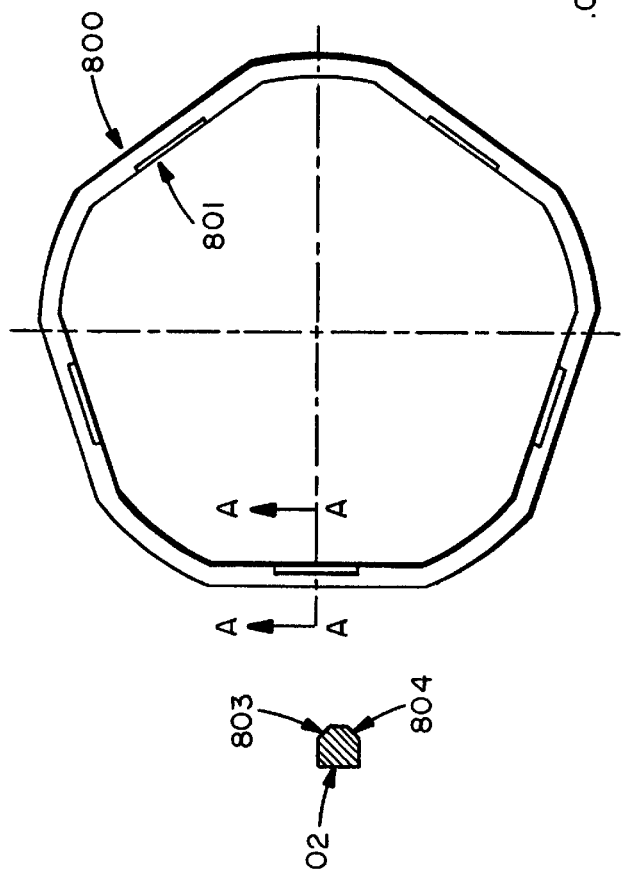
FIG. 8 depicts a top view of a closed penta shaped retaining ring with chamfers; fabricated at least in part using a polyaryletherketone material (shown on the right hand side of FIG. 8) and an exemplary cross sectional view of the aforementioned ring depicting the chamfer (shown on the left hand side of FIG. 8).

Ring size and shape optimization experiments continued. A wide variety of rings having were designed and tested, such as the closed chamfered penta shaped ring 800 depicted in FIG. 8 (an example of the chamfer being shown at 801). The right hand side of FIG. 8 depicts a top view of ring 800, which was fabricated at least in part using a polyaryletherketone material; and an exemplary cross sectional view 802 of ring 800 (with the section being taken along line A—A cut through ring 800) is shown on the left hand side of FIG. 8. Chamfer 801 is illustrated as 803 and 804 in the cross section.

Reference should now be made to FIGS. 9–12 which depict several of the other types of rings that were designed and tested.

Figure 9:
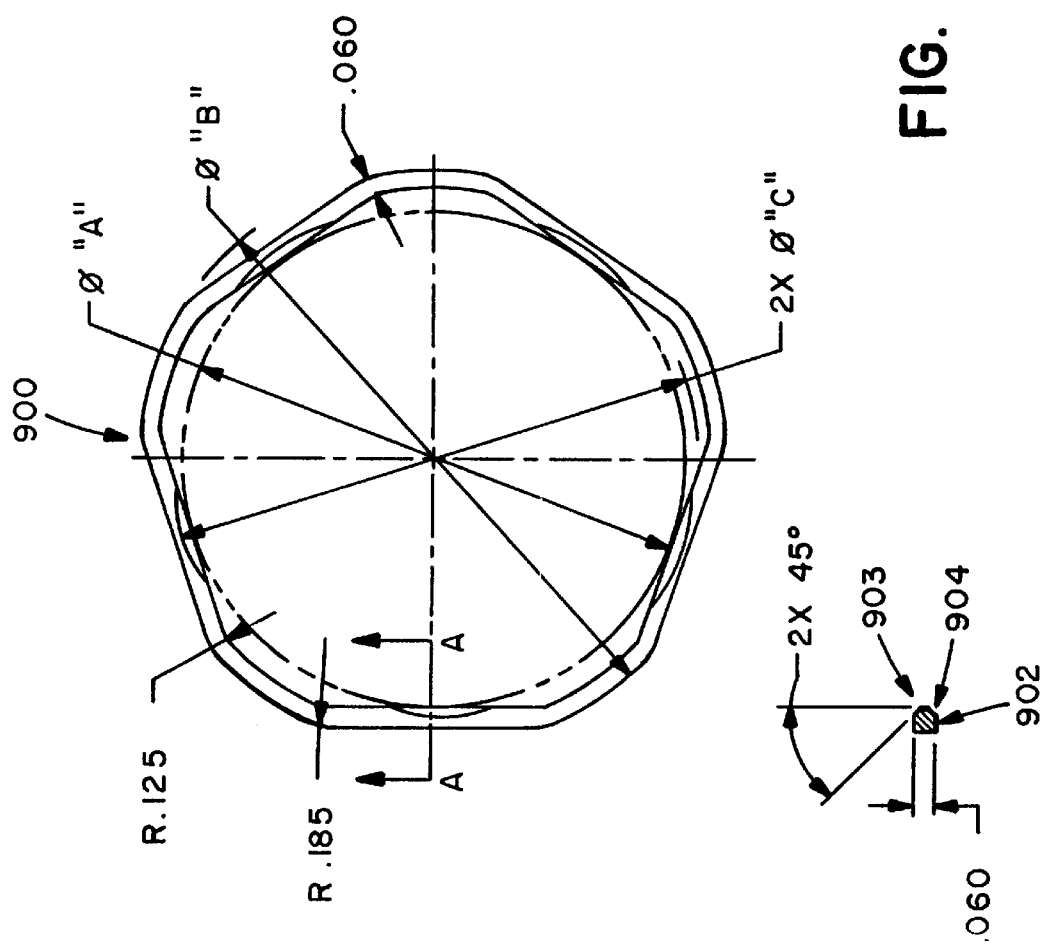
FIG. 9 depicts a top view of a closed penta shaped retaining ring with inside circular chamfers having varying diameters (as shown in the table included as part of FIG. 9), where the ring is fabricated at least in part using a polyaryletherketone material.

As indicated hereinbefore:

(1) FIG. 9 depicts a top view of a closed penta shaped retaining ring (shown as ring 900 in FIG. 9) with inside circular chamfers having varying diameters (as shown in table 901 included as part of FIG. 9), where the ring is fabricated at least in part using a polyaryletherketone material. FIG. 9 also depicts an exemplary cross sectional view 902 of ring 900 (with the section being taken along line A—A cut through ring 900), depicting inside circular chamfers 903 and 904.

Figure 10:
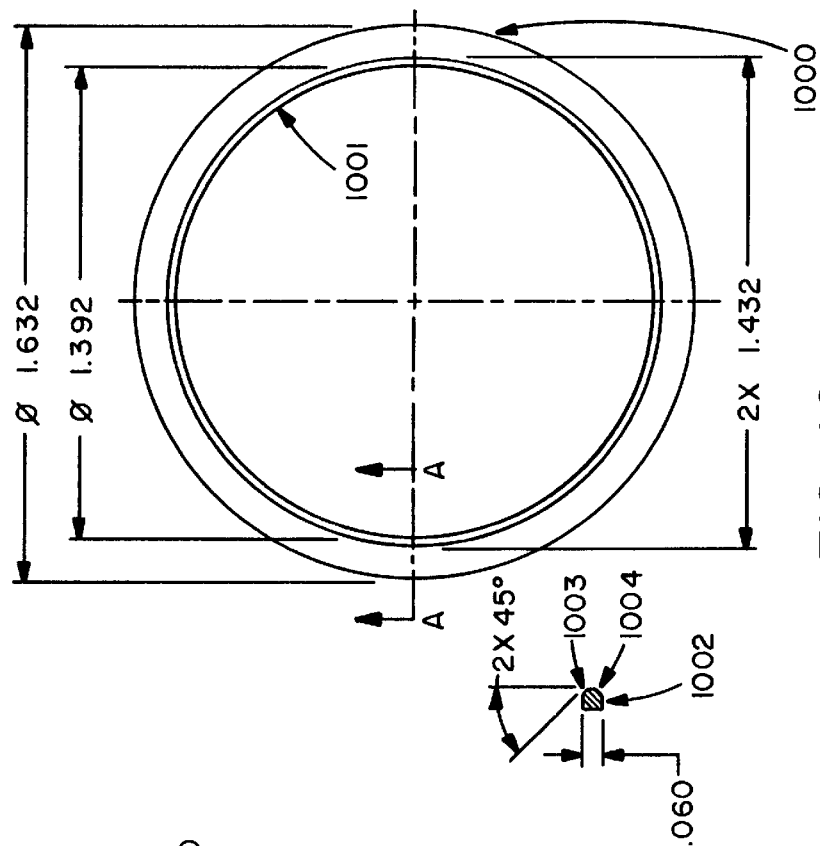
FIG. 10 depicts a top view of a closed circular retaining ring with an inside chamfer, fabricated at least in part using a polyaryletherketone material (shown on the right hand side of FIG. 10); and an exemplary cross sectional view of the aforementioned ring depicting the chamfer (shown on the left hand side of FIG. 10).

(2) FIG. 10 depicts a top view of a closed circular retaining ring (1000) fabricated at least in part using a polyaryletherketone material, having an inside chamfer 1001 (with ring 1000 being shown on the right hand side of FIG. 10); and an exemplary cross sectional view 1002 of ring 1000 (with the section being taken along line A—A cut through ring 1000), depicting inside chamfer 1001 at 1003 and 1004 in cross sectional view 1002. Cross sectional view 1002 of ring 1000 is shown on the left hand side of FIG. 10.

Figures 11, 12:
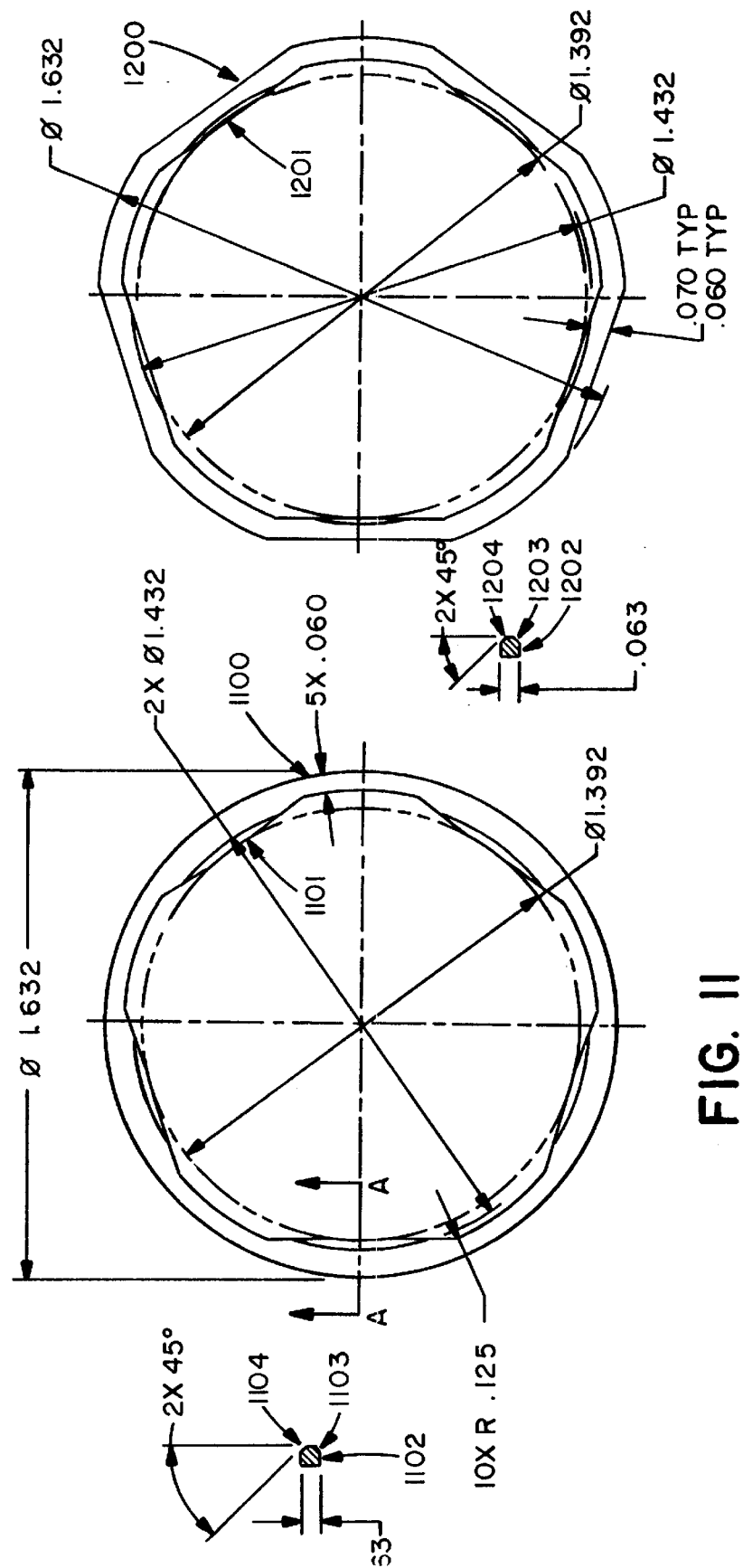
FIG. 11 depicts a top view of a closed circular retaining ring with an inside chamfer that is penta shaped, fabricated at least in part using a polyaryletherketone material (shown on the right hand side of FIG. 11); and an exemplary cross sectional view of the aforementioned ring depicting the chamfer (shown on the left hand side of FIG. 11).
FIG. 12 depicts a top view of a closed hex shaped retaining ring with an inside radial chamfer, where the ring is fabricated at least in part using a polyaryletherketone material (shown on the right hand side of FIG. 12); and an exemplary cross sectional view of the aforementioned ring depicting the chamfer (shown on the left hand side of FIG. 12).

(3) FIG. 11 depicts a top view of a closed circular retaining ring (1100) fabricated at least in part using a polyaryletherketone material, with an inside chamfer 1101 that is penta shaped (with ring 1100 being shown on the right hand side of FIG. 11); and an exemplary cross sectional view 1102 of ring 1100 (with the section being taken along line A—A cut through ring 1100), depicting inside chamfer 1101 at 1103 and 1104 in cross sectional view 1102. Cross sectional view 1102 of ring 1100 is shown on the left hand side of FIG. 11.

(4) FIG. 12 depicts a top view of a closed hex shaped retaining ring (1200) with an inside radial chamfer 1201 where ring 1200 (shown on the right hand side of FIG. 12) is fabricated at least in part using a polyaryletherketone material; and an exemplary cross sectional view 1202 of ring 1200 (shown on the left hand side of FIG. 12), depicting inside radial chamfer 1201 at 1203 and 1204.

A total of 36 rings were tested with the results improving using the ring designs depicted in FIGS. 9–12. Most push-in forces observed were very good, in the range of 13 kg to 20 kg. Different sizes and shapes had varied degrees of toggle, with push-out forces ranging from 2 kg. through 129 kg.

The experiments discussed hereinabove helped focus attention on the penta and hex shaped rings. Several more rings (all fabricated using PEEK), with different outside and inside diameters with two different band widths, were tested. Most assemblies were very tight depending on the outside and inside dimensions. The higher band widths seemed to increase the push-in and pull-out forces slightly. Push-out forces observed in the experiments conducted were very good, ranging from 20 kg to 163 kg.

The most promising data observed was for a hex shaped retaining ring (again fabricated using PEEK), having an outer diameter of 1.640" and an inner diameter of 1.365".

Such a ring is depicted in FIG. 13 where, as indicated hereinbefore, a top view of a closed hex shaped retaining ring 1300 with an inside radial chamfer 1301 is depicted. Ring 1300 is fabricated at least in part using a polyaryletherketone material and is shown on the right hand side of FIG. 13. An exemplary cross sectional view (1302) of ring 1300, depicting chamfer 1301 at 1303 and 1304, is shown on the left hand side of FIG. 13.

For a ring of the type illustrated by ring 1300, with a 0.060" band width, push-in forces of 23 kg, 21 kg and 20 kg were observed in three tests performed. Push-out forces observed were 82 kg, 66 kg and 163 kg.

For a 0.070" band width (with two tests performed), the push-in forces were 27 kg and 32 kg; and push-out forces were 66 kg and 140 kg.

As a result of the experiments described hereinabove, it was concluded that penta and hex shaped rings made at least in part using a polyaryletherketone material (like PEEK) were very well suited for use in acetabular cup assemblies.

It was further concluded after additional experimentation that rings made using composite materials, such as PEEK reinforced with carbon fiber, are particularly well suited for meeting the aforestated objectives of then invention, including, without limitation, being able to fabricate such rings in mass using well known injection molding processes, etc. More particularly, it was found that by adding a reinforcing material to the PEEK matrix the composite ring was strengthened and exhibited increased rigidity when compared with rings that were not reinforced.

According to the invention, an exemplary process for fabricating a locking mechanism to secure components of an acetabular cup assembly where the assembly includes an insert bearing component for receiving a femur ball and an outer shell component for attachment to an acetabulum to replace a natural hip socket, including a cavity for receiving the insert bearing component therein comprises the steps of: (a) forming a first arcuate groove on the outer surface of the insert bearing component; (b) forming a second arcuate groove on the inner surface of the outer shell component at a location that is axially aligned with the arcuate groove formed in the insert bearing component; and (c) fabricating a retaining ring for interlocking the insert into the outer shell, the retaining ring being formed at least in part using polyaryletherketone.

Further details of this process include utilizing a machining process to form the ring or alternatively utilizing an injection molding process to form the ring.

According to a preferred embodiment of the invention, the polyaryletherketone used in the aforementioned process is PEEK; and the finished ring (preferably 100% PEEK), when located simultaneously in the first arcuate groove and the second arcuate groove (to thereby interlock the insert and outer shell), has a finite number of contact points on both the insert and on the outer shell. According to alternate embodiments of the invention the polyaryletherketone used is combined with a reinforcing material, like carbon fiber, when added strength is required.

The invention also contemplates a process for fabricating a retaining ring for an acetabular cup assembly that includes (a) an insert bearing component having an inner bearing surface for receiving the ball and an outer surface formed to include an arcuate groove therein and (b) an outer shell component for attachment to an acetabulum to replace a natural hip socket, the outer shell component including an inner surface defining a cavity for receiving the insert bearing component therein, the inner surface of the outer shell component being formed to include an arcuate groove therein at a location that is axially aligned with the arcuate groove formed in the insert bearing components comprising the steps of: (a) creating a mold for the retaining ring having a predefined shaped which allows the ring, when formed, to be inserted into the arcuate groove of the outer shell component and simultaneously engage the insert bearing component, upon insertion of the insert bearing component into the outer shell component, by extending into the arcuate groove located on the outer surface of the insert bearing component; and (b) injecting a polyaryletherketone material into the mold.

What has been described in detail hereinabove are acetabular cup assemblies, locking mechanisms, retaining rings and processes for fabricating these devices, which meet all of the aforestated objectives. As previously indicated, those skilled in the art will recognize that the foregoing description has been presented for the sake of illustration and description only. It is not intended to be exhaustive or to limit the invention to the precise form disclosed, and obviously many modifications and variations are possible in light of the above teaching.

The embodiments and examples set forth herein were presented in order to best explain the principles of the instant invention and its practical application to thereby enable others skilled in the art to best utilize the instant invention in various embodiments and with various modifications as are suited to the particular use contemplated.

In view of the above it is, therefore, to be understood that the claims appended hereto are intended to cover all such modifications and variations which fall within the true scope and spirit of the invention.

What is claimed is:

1. A process for fabricating a retaining ring for an acetabular cup assembly that includes (a) an insert bearing component having an inner bearing surface for receiving said ball and an outer surface formed to include an arcuate groove therein and (b) an outer shell component for attachment to an acetabulum to replace a natural hip socket, the outer shell component including an inner surface defining a cavity for receiving said insert bearing component therein, said inner surface of said outer shell component being formed to include an arcuate groove therein at a location that is axially aligned with the arcuate groove formed in said insert bearing component, comprising the steps of:

(a) creating a mold for said retaining ring for an acetabular cup assembly having a predefined shaped which allows the ring, when formed, to be inserted into the arcuate groove of the outer shell component and simultaneously engage the insert bearing component, upon insertion of the insert bearing component into the outer shell component, by extending into the arcuate groove located on the outer surface of the insert bearing component; and (b) injecting a polyaryletherketone material into said mold.

2. A process as set forth in claim 1 wherein said polyaryletherketone is PEEK.

3. A process as set forth in claim 1 further comprising the step of:

(c) forming said ring as a circular shaped ring.

4. A process as set forth in claim 1 further comprising the step of:

(c) forming said ring as a split ring.

5. A process as set forth in claim 1 further comprising the step of:

(c) forming said ring as a closed ring.

6. A process as set forth in claim 1 further comprising the step of:

(c) combining said polyaryletherketone with a reinforcing material.

7. A process as set forth in claim 6 wherein said reinforcing material is carbon fiber.

8. A process for fabricating retaining rings used in acetabular cup assemblies for interlocking the components thereof, comprising the steps of:

(a) forming a mold to create acetabular cup assembly retaining rings having a predetermined shape enabling each such ring to extend simultaneously into a pair of grooves, each located in one of a pair of components being interlocked, using only a push-in force within a predefined range of push-in forces to combine said components and the ring; and (b) injecting polyaryletherketone material into said mold as part of an injection molding process to create the retaining rings having said predetermined shape.

9. A process as set forth in claim 8 wherein said predetermined shape is such that only a predetermined amount of pull-out force within a predefined range of pull-out forces is required to separate said pair of components and ring once interlocked.

* * * * *

UNITED STATES PATENT AND TRADEMARK OFFICE
CERTIFICATE OF CORRECTION

PATENT NO. : 5,964,809
DATED : October 12, 1999
INVENTOR(S) : Lin et al.

It is certified that error appears in the above-identified patent and that said Letters Patent is hereby corrected as shown below:

Column 1, line 45, "fibers" should read --fiber--.
Column 5, line 54, "fibers" should read --fiber--.
Column 5, line 58, "particulars" should read --particular--.
Column 9, line 2, after "ring", insert --,--.
Column 9, line 67, "weight" should read --Weight--.

Signed and Sealed this

Nineteenth Day of December, 2000

Attest:

Q. TODD DICKINSON

Attesting Officer

Commissioner of Patents and Trademarks